(12) United States Patent
King

(10) Patent No.: US 6,218,421 B1
(45) Date of Patent: Apr. 17, 2001

(54) METHOD OF PROMOTING SMOKING CESSATION

(75) Inventor: Stephen Eldon King, Hertfordshire (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/346,402

(22) Filed: Jul. 1, 1999

(51) Int. Cl.⁷ .................. A61K 31/4015; C07D 209/40; C07D 209/34; A61K 31/4035
(52) U.S. Cl. .................. 514/421; 514/813; 514/958; 548/486; 548/493; 206/569
(58) Field of Search .................. 514/813, 421, 514/958; 548/493, 486; 206/569

(56) References Cited

U.S. PATENT DOCUMENTS

| | | | |
|---|---|---|---|
| 3,598,824 | * 8/1971 | Troxler et al. | 514/813 X |
| 4,452,808 | * 6/1984 | Gallagher | 424/274 |
| 4,575,510 | * 3/1986 | Sjoerdsma | 514/401 |
| 4,588,740 | * 5/1986 | Gallagher | 514/418 |
| 4,800,204 |   1/1989 | Mueller et al. | 514/267 |
| 4,824,860 | * 4/1989 | Owen | 514/418 |
| 4,912,126 | * 3/1990 | Owen | 514/418 |
| 4,997,954 | * 3/1991 | Fortunak | 548/486 |
| 5,039,680 | * 8/1991 | Imperato et al. | 514/304 |
| 5,204,340 | * 4/1993 | Flaugh et al. | 514/210 |
| 5,336,781 | * 8/1994 | Giles et al. | 548/486 |
| 5,747,512 | * 5/1998 | Keenan et al. | 514/343 |

* cited by examiner

*Primary Examiner*—Floyd D. Higel
(74) *Attorney, Agent, or Firm*—Loretta Henderson; Stephen Venetianer; Charles Kinzig

(57) ABSTRACT

A method for promoting smoking cessation, which method comprises administrating an effective, non-toxic amount of ropinirole or a pharmaceutically acceptable salt or solvate thereof to a human in need thereof. Said ropinirole is preferably administered orally or transdermally. Also provided is a medicament for use in smoking cessation that comprises ropinirole. Said medicament may be a tablet for oral use or a transdermal patch containing ropinirole.

13 Claims, No Drawings

METHOD OF PROMOTING SMOKING CESSATION

FIELD OF THE INVENTION

The present invention relates to a method for smoking cessation treatment, and especially to the use of ropinirole in such treatment.

BACKGROUND OF THE INVENTION

Pharmaceutical products with antihypertensive and antianginal properties are described in U.S. Pat. No. 4,452,808 and U.S. Pat. No. 4,588,740. An especially important compound among those disclosed is 4-[2-(di-n-propylamino) ethyl]-1,3-dihydro-2H-indolin-2-one hydlochlorid (ropinirole). This compound has also been found to be a potent CNS active non-ergot dopamine receptor agonist (see U.S. Pat. No. 4,824,860 and U.S. Pat. No. 4,912,126). The hydrochloride salt of ropinirole is approved for human use in therapy to treat Parkinson's disease.

Processes for the production of ropinirole hydrochloride are disclosed in U.S. Pat. No. 4,997,954 and U.S. Pat. No. 5,336,781.

Bromocriptine, another anti-Parkinson's drug, has been proposed for use in controlling tobacco use (see U.S. Pat. No. 4,800,204). Bromocriptine, however is an ergot alkaloid and has a number of well known side effects.

OBJECTS OF THE INVENTION

An object of the present invention is to provide an improved method of treating smoking addiction.

Another object of the present invention is to provide a method of smoking cessation treatment which avoids the administration of an ergot alkaloid.

It has been surprisingly discovered that ropinirole has potential therapeutic utility as a medicament for smoking cessation treatment.

SUMMARY OF THE INVENTION

Accordingly, the present invention provides a method for promoting smoking cessation, which method comprises administering an effective, non-toxic amount of ropinirole or a pharmaceutically acceptable salt or solvate thereof, to an human in need thereof.

The present invention also provides the use of ropinirole or a pharmaceutically acceptable salt or solvate thereof in the manufacture of a medicament for use in smoking cessation treatment.

Ropinirole used in the present invention is suitably in the form of the free base or a pharmaceutically acceptable salt thereof. A preferred pharmaceutically acceptable salt of ropinirole is crystalline hydrochloride. Suitable procedures for preparing ropinirole hydrochloride include those mentioned in U.S. Pat. No. 4,997,954, and preferably those mentioned in U.S. Pat. No. 5,336,781.

A medicament for use in smoking cessation treatment may be prepared by a mixture of ropinirole or a pharmaceutically acceptable salt or solvate thereof with an appropriate carrier, which may contain a diluent, binder, filler, disintegrant, flavouring agent, colouring agent, lubricant or preservative in conventional manner.

Preferably, the medicament is in unit dosage form. For example, such preparations may be in a pack form accompanied by written or printed instructions for use as a smoking cessation treatment.

The suitable dosage range for ropinirole or a pharmaceutically acceptable salt or solvate depends on the severity of the smoking disorders and on the condition of the patient. It will also depend, inter alia, upon the relation of potency to absorbability and the frequency and route of administration.

Typically the human in need of treatment in accordance with this invention will not be suffering from Parkinson's disease and/or will not be receiving treatment for Parkinson's disease using ropinirole.

DETAILED DESCRIPTION OF THE INVENTION

Ropinirole or a pharmaceutically acceptable salt or solvate thereof may be formulated for administration by any route, and examples are oral, sub-lingual, transdermal, rectal, topical, parenteral, intravenous or intramuscular administration. Preparations may, if desired, be designed to give slow release of the ropinirole or a pharmaceutically acceptable salt or solvate thereof.

The medicaments may, for example, be in the form of tablets, capsules, sachets, vials, powders, granules, lozenges, reconstitutable powders, or liquid preparations, for example solutions or suspensions, or suppositories.

In a preferred embodiment, said medicament is provided in the form of a transdermal patch. Said patch may comprise a reservoir containing ropinirole or a pharmaceutically acceptable salt or solvate thereof and means for applying the reservoir in drug-transmitting relation to the skin or a membrane of a patient. Said reservoir may be adapted to be placed in direct contact with the skin or membrane, or a rate-controlling membrane may be interposed between the reservoir and the skin or membrane. Said patch may further comprise an impermeable backing layer which overlays or envelops the reservoir remote from the skin or membrane, and an adhesive layer may be provided around the reservoir or between the reservoir and the skin for securing the patch to a patient.

Said reservoir may contain ropinirole or a pharmaceutically acceptable salt or solvate thereof in liquid form or as a solution as herein described. Alternatively said reservoir may comprise a solid or semi-solid polymer matrix having ropinirole homogeneously or heterogeneously dispersed or dissolved therein. Said ropinirole may be provided in the reservoir at an activity of 1.0. Said reservoir may further include a skin permeation enhancing agent that is adapted to be co-delivered with said ropinirole.

The medicaments, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycerine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid medicaments may be obtained by conventional methods of blending, filling, tabletting or the like. Repeated blending operations may be used to distribute ropinirole or a salt or solvate thereof throughout those medicaments employing large quantities of fillers. When the medicament is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The medicament may also be in the form of an ingestible capsule, for example of gelatin containing ropinirole or a salt thereof if desired with a carrier or other excipients.

Medicaments for oral administration as liquids may be in the form of, for example, emulsions, syrups, or elixirs, or may be presented as a dry product for reconstitution with water or other suitable vehicle before use. Such liquid medicaments may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

Ropinirole or a pharmaceutically acceptable salt or solvate thereof may also be administered by a non-oral route. In accordance with routine pharmaceutical procedure, the medicaments may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

As mentioned hereinbefore, the effective dose of the ropinirole or pharmaceutically acceptable salt or solvate depends on the severity of the smoking disorders to be treated, the condition of the patient and on the frequency and route of administration.

Preferably, the composition is administered in the form of one or more dosage units. Each dosage unit for oral administration may comprise from 0.1 to 50 mg of ropinirole; preferably 0.25–10 mg, more preferably 0.25–5 mg, e.g. 0.25 mg, 0.5 mg, 1 mg, 2 mg, 3 mg, 4 mg and 5 mg. For parenteral administration, each dosage unit may comprise from 0.1 to 15 mg of ropinirole, preferably 0.25–10 mg and more preferably 0.25–5 mg.

The daily dosage required for an adult patient may, for example, be an oral dosage of between 0.1 mg and 100 mg, preferably between 0.25 mg and 25 mg, more preferably 0.25–15 mg; or an intravenous, subcutaneaus or intramuscular dosage of between 0.1 mg and 25 mg, preferably between 0.1 mg and 15 mg, of ropinirole. The compound may be administered 1 to 4 times per day. Suitably the compound will be administered for a period of continuous therapy. By way of example, typical regimens may comprehend the administration of 0.25–5 mg or 0.25–2 mg of ropinirole 2 or 3 times a day.

In some preferred embodiments, the present invention is practised using a controlled release or delayed release formulation containing ropinirole or a pharmaceutically acceptable salt or solvate thereof.

By 'controlled release' is meant any formulation technique wherein release of the active substance from the dosage form is modified to occur at a slower rater than that from an immediate release product, such as a conventional swallow tablet or capsule.

By 'delayed release' is meant any formulation technique wherein release of the active substance from the dosage form is modified to occur at a later time than that from a conventional immediate release product. The subsequent release of active substance from a delayed release formulation may also be controlled as defined above.

Examples of controlled release formulations which are suitable for incorporating ropinirole are described in:

Sustained Release Medications, Chemical Technology Review No. 177. Ed. J. C. Johnson. Noyes Data Corporation 1980; and Controlled Drug Delivery, Fundamentals and Applications, 2nd Edition. Eds. J. R. Robinson, V. H. L. Lee. Mercel Dekkes Inc. New York 1987.

Examples of delayed release formulations which are suitable for incorporating ropinirole are described in:

Remington's Pharmaceutical Sciences 16th Edition, Mack Publishing Company 1980, Ed. A. Osol.

Such controlled release formulations are preferably formulated in a manner such that release of active substance such as ropinirole is effected predominantly during the passage through the stomach and the small intestine, and delayed release formulations are preferably formulated such that release of active substance such as ropinirole is avoided in the stomach and is effected predominantly during passage through the small intestine.

Said formulations are preferably formulated such that the release of the active substance predominantly occurs 1½ to 3 hours post ingestion.

Preferred formulations are ultimately enteric coated tablets or caplets, wax or polymer coated tablets or caplets or time-release matrices, or combinations thereof.

Thus, a particular aspect of the invention involves use of a polymeric controlled release composition comprising a reaction complex formed by the interaction of (1) a calcium polycarbophil component which is a water-swellable, but water insoluble, fibrous cross-linked carboxy-functional polymer, said polymer containing (a) a plurality of repeating units of which at least about 80% contain at least one carboxyl functionality, and (b) about 0.05 to about 1.5% cross-linking agent substantially free from polyalkenyl polyether, said percentages being based upon the weights of unpolymerised repeating unit and cross-linking agent, respectively, with (2) water, in the presence of ropinirole. The amount of calcium polycarbophil present is from about 0.1 to about 99% by weight, for example about 10%. The amount of active agent present is from about 0.0001 to about 65% by weight, for example between about 5 and 20%. The amount of water present is from about 5 to about 200% by weight, for example between about 5 and 10%. The interaction is carried out at a pH of between about 3 and about 10, for example about 6 to 7. The calcium polycarbophil is originally present in the form of a calcium salt containing from about 5 to about 25% calcium.

Thus, a further particular aspect involves use of a system for the controlled release of ropinirole, comprising (a) a deposit-core comprising an effective amount of ropinirole and having defined geometric form, and (b) a support-platform applied to said deposit-core, wherein said deposit-core contains ropinirole, and at least one member selected from the group consisting of (1) a polymeric material which swells on contact with water or aqueous liquids and a gellable polymeric material wherein the ratio of the said swellable polymeric material to said gellable polymeric material is in the range 1:9 to 9:1, and (2) a single polymeric material having both swelling and gelling properties, and wherein the support-platform is an elastic support, applied to said deposit-core so that it partially covers the surface of the deposit-core and follows changes due to hydration of the deposit-core and is slowly soluble and/or slowly gellable in aqueous fluids. The support-platform may comprise polymers such as hydroxypropylmethylcellulose, plasticizers such as a glyceride, binders such as polyvinylpyrrolidone, hydrophilic agents such as lactose and silica, and/or hydrophobic agents such as magnesium stearate and glycerides. The polymer(s) typically make up 30 to 90% by weight of the support-platform, for example about 35 to 40%. Plasticizer may make up at least 2% by weight of the support-platform, for example about 15 to 20%. Binder(s), hydrophilic agent(s) and hydrophobic agent(s) typically total up to about 50% by weight of the support-platform, for example about 40 to 50%.

The present invention further provides a pharmaceutical composition for use in smoking cessation treatment which comprises an effective amount of ropinirole or a pharmaceutically acceptable salt or solvate thereof and a pharmaceutically acceptable carrier. Such compositions may be prepared in the manner as hereinbefore described.

What is claimed is:

1. A method for promoting cessation of smoking tobacco, which method comprises administering an effective, non-toxic amount of ropinirole or a pharmaceutically acceptable salt or solvate thereof to a human in need thereof.

2. A method as claimed in claim 1, wherein ropinirole is administered in the form of the free base or a pharmaceutically acceptable salt or solvate thereof.

3. A method as claimed in claim 1 wherein the pharmaceutically acceptable salt is the crystalline hydrochloride.

4. A method as claimed in claim 1 wherein ropinirole is administered orally, sub-lingually, rectally, topically, parenterally, intraveneously or intramuscularly.

5. A method as claimed in claim 1 wherein ropinirole is administered transdermally.

6. A method as claimed in claim 1 wherein ropinirole is administered to said human for a period of continuous therapy.

7. A method as claimed in claim 6 wherein a daily dosage amount of 0.1–100 mg of ropinirole is administered to said human.

8. A method according to claim 1 wherein ropinirole or its pharmaceutically acceptable salt is administered in the form of one or more dosage units.

9. The method of claim 1, wherein ropinirole is administered to the human in the form of 1–4 separate doses per day.

10. A method according to claim 8 wherein ropinirole is in a controlled release or delayed release formulation.

11. The method of claim 6, wherein the human is given a daily dosage of 0.25–15 mg of ropinirole or a pharmaceutically acceptable salt or solvate thereof.

12. The method of claim 6, wherein the human is given a daily dosage of 0.25–10 mg of ropinirole or a pharmaceutically acceptable salt or solvate thereof.

13. The method of claim 6, wherein the human is given a daily dosage of 0.25–5 mg of ropinirole or a pharmaceutically acceptable salt or solvate thereof.

* * * * *